| United States Patent [19] | [11] | 4,351,753 |
|---|---|---|
| Kaneko | [45] | Sep. 28, 1982 |

[54] LIQUIFIED NORMALLY SOLID POLYOXYALKYLENE BLOCK COPOLYMERS

[75] Inventor: Thomas M. Kaneko, Trenton, Mich.

[73] Assignee: BASF Wyandotte Corporation, Wyandotte, Mich.

[21] Appl. No.: 200,118

[22] Filed: Oct. 24, 1980

[51] Int. Cl.³ .............................................. C08L 63/00
[52] U.S. Cl. .................................. 252/357; 252/351; 252/352; 568/613; 568/620; 524/612; 524/386
[58] Field of Search ............... 260/29.2 EP, 33.4 EP; 525/409; 106/15 R; 252/352; 568/613, 619, 620; 528/496; 424/78

[56] References Cited

U.S. PATENT DOCUMENTS

| 2,602,780 | 7/1952 | Zisman et al. | 106/14.15 |
| 2,674,619 | 4/1954 | Lundsted | 260/29.6 ME |
| 2,677,700 | 5/1954 | Jackson et al. | 260/29.6 ME |
| 2,979,528 | 4/1961 | Lundsted | 252/110 |
| 3,036,118 | 5/1962 | Jackson et al. | 560/182 |
| 3,945,964 | 3/1976 | Hastings et al. | 260/29.2 EP |
| 4,089,814 | 5/1978 | Schmolka | 424/78 |

*Primary Examiner*—Theodore E. Pertilla
*Attorney, Agent, or Firm*—Bernhard R. Swick

[57] ABSTRACT

This invention relates to liquified normally solid forms of polyoxyalkylene block copolymers particularly suitable for use in pesticide concentrates comprising a normally solid polyoxyalkylene block copolymer nonionic surface-active agent and ethylene glycol with or without water.

18 Claims, No Drawings

LIQUIFIED NORMALLY SOLID POLYOXYALKYLENE BLOCK COPOLYMERS

BACKGROUND OF THE INVENTION

1. Field of the Invention

This invention relates to liquified normally solid forms of polyoxyalkylene block copolymers. The compositions of this invention are particularly useful in flowable pesticide concentrates.

2. Description of the Prior Art

Pesticidally-active compounds have conventionally been formulated as emulsifiable concentrates or as wettable powders. The emulsifiable concentrates have normally been the type of formulation preferred for pesticides which are soluble in organic solvents. Pesticides with limited solvent solubility have usually been formulated as wettable powders. Both of these formulation types present their own special problems.

Emulsifiable concentrates are based on one of our diminishing natural resources—petroleum. Because large amounts of solvents are required, emulsifiable concentrates can only become more expensive as time goes on. In addition to the economic considerations, it is becoming increasingly apparent that conservation of this valuable resource is imperative.

Wettable powders are dusty and breathing the dust can cause skin and eye irritation as well as illness. Disposal of the residue containing bag is also of growing concern, because children and those unfamiliar with the potential hazards might be exposed when the bag is discarded.

As a result of these problems, flowable formulations are becoming increasingly more prevalent. They are prepared by dispersing the finely divided pesticide ingredients in an aqueous medium to form a concentrated dispersion. For application this dispersion is further diluted with water. Flowable formulations provide the following advantages: little or no organic solvent required, virtual elimination of inhalation danger, and greatly reduced skin and eye irritation problems. In addition, container residues can easily be hosed into the spray tank prior to disposing the container.

The applications of polyoxyalkylene block copolymers, especially polyols containing high amounts of ethylene oxide, have been widely recognized and used as effective emulsifiers for pesticide concentrates. Because of their high ethylene oxide contents, these polyols are either paste or solid products, making their uses in formulating agricultural products cumbersome and very difficult, due to gel formation upon addition of water. In accordance with the prior art, it was discovered that certain alcohol ethoxylates, such as tridecyl alcohol, 6 mole ethoxylate or $C_{18}$ alcohol 20 mole ethoxylate, plus water, are good solvents. However, agricultural chemical formulators have discovered that such alcohol ethoxylates are detrimental to long term stability of the pesticide concentrate. Further, the prior art compositions have presented problems related to gelling and often have viscosities that are too high to be readily pumpable from around room temperature, i.e., 20° to 25° C. up to 50° C.

It has generally been believed, in accordance with the prior art, that to solubilize high ethylene oxide content polyols and prevent gel formation, the polyol must be added in small amounts, or incrementally, to *chilled* water, because water at room temperature or higher would cause gel formation.

Accordingly, it is a purpose of the instant invention to provide liquid compositions useful in pesticide concentrates which are readily pumpable at temperatures below 50° C. and particularly at or about room temperature, which are non-gelling and which possess long term stability.

SUMMARY OF THE INVENTION

In accordance with the instant invention, it has been discovered that the above objects may be achieved by liquid compositions useful in pesticide concentrates comprising a normally solid polyoxyalkylene block copolymer nonoinic surface-active agents and ethylene glycol with or without water. As used herein, the expression "normally solid" includes the paste form. It has been found also in accordance with the instant invention that these normally solid nonionic polyoxyalkylene block copolymers dissolve readily in ethylene glycol at a temperature of about 170° F. or higher (170° F. is about 77° C.). The use of temperatures lower than 170° F. results in formation of "scum" or gel formation whereas no scum or gel whatsoever is formed at 170° F. or higher. Also, subsequent addition of water to the nonionic copolymer/glycol blend held at 170° F. did not form any scum or gel. There is no known upper temperature limit other than one of economics, i.e., the cost of heating.

DETAILED DESCRIPTION OF INVENTION

The emulsifier of the instant invention comprises from about 15 to 90 percent by weight normally solid nonionic polyoxyalkylene block copolymer, 15 to 80 percent by weight ethylene glycol and 0 to 30 percent by weight of water. The preferred composition comprises from about 20 to 80 percent by weight polyoxyalkylene block copolymer, 20 to 60 percent by weight ethylene glycol and 5 to 20 percent by weight water.

Suitable nonionic surface active agents are cogeneric mixtures of conjugated polyoxyalkylene compounds containing in their structure the residue of an active hydrogen containing compound having from 1 to 6 carbon atoms and at least one hydrophobic oxyalkylene chain in which the oxygen/carbon atom ratio does not exceed 0.40 and at least one hydrophilic oxyalkylene chain in which the oxygen/carbon atom ratio is greater than 0.40.

Polymers of oxyalkylene groups obtained from propylene oxide, butylene oxide, amylene oxide, styrene oxide, mixtures of such oxyalkylene groups with each other and with minor amounts of polyoxyalkylene groups obtained from ethylene oxide, butadiene dioxide, and glycidol are illustrative of hydrophobic oxyalkylene chains having an oxygen/carbon atom ratio not exceeding 0.40. Polymers of oxyalkylene groups obtained from ethylene oxide, butadiene dioxide, glycidol, mixtures of such oxyalkylene groups with each other and with minor amounts of oxyalkylene groups obtained from propylene oxide, butylene oxide, amylene oxide and styrene oxide are illustrative of hydrophilic oxyalkylene chains having an oxygen/carbon ratio greater than 0.40.

Among the conjugated polyoxyalkylene compounds which can be used in the compositions of the invention are those which correspond to the formula:

$$Y[(C_3H_6O)_n(C_2H_4O)_mH]_x$$

wherein Y is the residue of an organic compound having from about 1 to 6 carbon atoms and containing x reactive hydrogen atoms in which x has a value of at least one, m has a value such that the oxyethylene content of the molecule is from about 20 to 90 weight percent and n has a value such that the total molecular weight of the polyoxypropylene groups is from about 950 to 4000. Compositions of this type are more particularly described in U.S. Pat. Nos. 2,674,619 and 2,677,700.

Other suitable nonionic block copolymers which correspond to the formula:

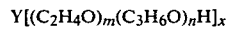

$$Y[(C_2H_4O)_m(C_3H_6O)_nH]_x$$

wherein Y, n, m and x have values as set forth above. Compositions of this type are more particularly described in U.S. Pat. No. 3,036,118. In either of the above formulas, compounds falling within the scope of the definition for Y include, for example, propylene glycol, ethylene glycol, diethylene glycol, glycerine, pentaerythritol, trimethylolpropane, ethylene diamine and the like. Also, the oxypropylene chains optionally, but advantageously, contain small amounts of ethylene oxide and the oxyethylene chains also optionally, but advantageously, contain small amounts of alkylene oxides such as propylene oxide and butylene oxide.

Preferred compounds of the above type are those wherein Y is the residue of propylene glycol or ethylene glycol and x is 2. In all cases, the compounds of this invention are those which are normally solid as defined above. Whether or not the product is a solid rather than a liquid varies, not only with the percent oxyethylene groups in the compound, but also with the molecular weight of the polyoxypropylene groups. More specifically, where the molecular weight of the polyoxypropylene groups in the first formula is 950, the percent oxyethylene groups should be greater than 55 percent. On the other hand, where the molecular weight of the polyoxypropylene groups is 4000, the percent of oxyethylene groups must be greater than 20. With respect to the second formula set forth above, it is most preferred to employ compounds wherein the total molecular weight of the polyoxypropylene hydrophobic units ranges from 1000 to 3100. Where the molecular weight of the polyoxypropylene groups is 1000, the percent oxyethylene groups should exceed 55, whereas when the total molecular weight of the polyoxypropylene groups is 3100, the percent polyoxyethylene groups should exceed 25 percent.

Other suitable nonionic surface-active block copolymers are those where Y, in the above formulas, is the residue of a nitrogen-containing reactive hydrogen compound having 1 to 6 carbon atoms per molecule and most preferably where Y is the residue of ethylene diamine and x is 4. Such compounds contain adjoined to the nitrogens of the ethylene diamine, oxypropylene units and oxyethylene units. The oxypropylene units may be adjoined to the nitrogens of the ethylene diamine and outboard of said oxypropylene units are oxyethylene units. Products of this type are described in U.S. Pat. No. 2,979,528. The oxypropylene units would preferably have a molecular weight of 500 to 7000 and the oxyethylene units would range from approximately 25 to 80 weight percent of the compound. However, this varies with the molecular weight of the polyoxypropylene units, i.e., where the molecular weight of the polyoxypropylene units is 500, the weight percent ethylene oxide units should exceed 65 percent, whereas, where the molecular weight of the oxypropylene units is 7000, the oxyethylene units should exceed 25 percent by weight.

As with the formulas set forth above, the oxyethylene units can be adjoined to the nitrogens with the oxypropylene units outboard of said oxyethylene units.

The invention is illustrated by the following specific examples, which are to be taken as illustrative and not in a limiting sense. In the examples, parts are by weight unless otherwise specifically indicated, and temperatures are in degrees centigrade.

In the examples, the pour point was determined as follows:

A heat-treated glass tube, 13 centimeters high, with internal diameter of 28 millimeters and an external diameter of 32 millimeters is filled to the 8 centimeter level with the sample. The tube is then placed in a dry ice-acetone bath, a thermometer is placed in the tube, and the sample stirred with the thermometer. The tube is removed from the bath approximately every 10 to 15 seconds and checked to see if the product is still pourable, checking with the thermometer to be sure the product is at a uniform temperature throughout. Each time the tube is removed from the bath, it is checked by tilting to see if the product in the tube is pourable. When it reaches the point where it is barely pourable, the temperature is read on the thermometer. Five degrees F is then added to the temperature reading as a safety factor and this is recorded as the pour point.

The Brookfield viscosity for the examples below was determined as follows:

The Brookfield viscometer rotates a spindle in the liquid and measures the torque necessary to overcome the resistance to the induced movement at a specific temperature. More specifically, the sample to be tested is placed in a 250 milliliter beaker. The sample should be obtained in the sample container used for the test to avoid any necessity for mixing the sample before testing and reducing the possibility of air bubble inclusion and then is allowed to stand until any occluded air bubbles have disappeared. The sample and container are then placed in a water bath which is maintained at a constant temperature of 25° C. ±0.1° C. in such a manner that the sample level is below the level of the bath. The preferred spindle, which is spindle No. 3 for the following examples is attached to a Brookfield viscometer, Model LVF. This is a well-known device to the skilled in the art and is readily available on the market. The spindle is inserted into the sample and the viscometer is allowed to run at specified speed for 10 to 20 turns and then stopped and the viscosity recorded.

EXAMPLE 1

A composition in accordance with the present invention is prepared by adding 60 parts by weight ethylene glycol to a reactor equipped for heating, cooling and mixing. The ethylene glycol is agitated and heated to 80° C. and controlled to ±5° C. Twenty-one parts of a nonionic block copolymer, referred to herein as Nonionic No. 1, is charged to the reactor at 80° C.±5° C., with continued stirring. Nonionic No. 1 defines a block copolymer which is the polyoxyethylene adduct of a polyoxypropylene hydrophobic base, i.e., comprises polyoxyethylene groups at both ends of a polyoxypropylene base. The molecular weight of the hydrophobic base is about 3250 and the oxyethylene content is about 50 weight percent of the molecule. In stirring, the creation of a vortex is avoided since this tends to cause foaming. Agitation is continued until the mixture is uniform. Heating is then discontinued and 19 parts by weight of city water at the temperature of the water line is added and agitation continued until the product is uniform. The rate of agitation must be such as to avoid foaming. The material is then poured from the reactor into drums at a temperature of about 20° C. to 60° C.

The product has a specific gravity of 1.076. The Brookfield viscosities using spindle No. 3 at an rpm of 30 were 324 cps at 25° C. and 112 cps at 50° C.

EXAMPLES 2 and 3

Two compositions were prepared as described above for Example 1. However, samples were taken after stirring one hour, two hours, and three hours for Example 2 and one hour and two hours for Example 3. The pour point and Brookfield viscosity for each sample from each example is shown in Table I below along with the specific gravities for Example 3.

TABLE I

| Example | 2 | 2 | 2 | 3 | 3 |
|---|---|---|---|---|---|
| Mixing Time (hr.) | 1 | 2 | 3 | 1 | 2 |
| Pour Pt. | 41.5° F. | 42.4° F. | 49.6° F. | 51.4° F. | 51.4° F. |
|  | 5.3° C. | 5.8° C. | 9.8°C. | 10.8° C. | 10.8° C. |
| Specific Gravity @25° C. | — | — | — | 1.083 | 1.080 |
| Brookfield Viscosity |  |  |  |  |  |
| @25° C. (cps) | 388 | 344 | 356 | 356 | 356 |
| @50° C. (cps) | 120 | 112 | 116 | 116 | 124 |

EXAMPLES 4–13

Ten compositions, in accordance with the instant invention, are prepared in the manner described in Example 1 from the compositions shown in Table II below. The specific gravities of the resulting product and the Brookfield viscosities using No. 3 spindle at 30 rpm at varying temperatures are also shown in Table II below.

In the Table II, Nonionic No. 2 defines the polyoxyethylene adduct of a polyoxypropylene hydrophobic base having a molecular weight of the hydrophobic base of about 1750 wherein the oxyethylene content is about 50 weight percent of the molecule.

TABLE II

| Example No. | 4 | 5 | 6 | 7 | 8 | 9 | 10 | 11 | 12 | 13 |
|---|---|---|---|---|---|---|---|---|---|---|
| Formulation, % by wt. |  |  |  |  |  |  |  |  |  |  |
| Ethylene Glycol | 60 | 50 | 40 | 30 | 20 | 60 | 56 | 56 | 61 | 53 |
| Nonionic No. 2 | 40 | 50 | 60 | 70 | 80 | 21 | 25 | 30 | 25 | 33 |
| Water | — | — | — | — | — | 19 | 19 | 14 | 14 | 14 |
| Properties |  |  |  |  |  |  |  |  |  |  |
| Specific Gravity |  |  |  |  |  |  |  |  |  |  |
| @25° C. (cps) | 1.080 | 1.076 | 1.068 | 1.061 | 1.056 | — | — | — | — | 1.072 |
| Brookfield Viscosity |  |  |  |  |  |  |  |  |  |  |
| @20° C. | — | 716 | 648 | 2360 | 856 | 75 | 146.6 | 356 | 162 | 656 |
| @25° C. | 396 | 460 | 508 | 524 | 632 | — | — | — | — | — |
| @30° C. | — | 412 | 420 | 416 | 492 | 49 | 88.2 | 197 | 102 | 328 |
| @40° C. | — | 224 | 248 | 292 | 292 | 35.6 | 66 | 133 | 67.4 | 248 |
| @50° C. | — | 152 | 164 | 188 | 208 | 26.8 | 49.8 | 88.4 | 48 | 152 |

EXAMPLE 14

A composition in accordance with the instant invention is prepared as described in Example 1 with the exception that the polyoxypropylene adduct of a polyoxyethylene base, i.e., comprises polyoxypropylene groups at both ends of a polyoxyethylene base, is substituted for Nonionic No. 1. The oxyethylene content is about 40 weight percent of the molecule and the polyoxypropylene hydrophobic groups have a molecular weight of about 3100. The product is readily pumpable at temperatures below 50° C., including room temperature, and possesses long term stability.

EXAMPLE 15

A composition in accordance with the instant invention is prepared as described in Example 1 with the exception that the polyoxyethylene adduct of a polyoxypropylene-ethylene diamine condensate is substituted for Nonionic No. 1. The oxypropylene hydrophobic base has a molecular weight of about 5000 and the oxyethylene content is about 40 weight percent of the molecule. The product is readily pumpable at temperatures below 50° C., including room temperature, and possesses long term stability.

EXAMPLE 16

A composition in accordance with the instant invention is prepared as described in Example 1 with the exception that the polyoxypropylene adduct of a polyoxyethylene-ethylene diamine condensate is substituted for Nonionic No. 1. The oxypropylene groups have a molecular weight of about 1500 and the oxyethylene content is about 70 percent by weight of the molecule. The product is readily pumpable at temperatures below 50° C., including room temperature, and possesses long term stability.

While there has been shown and described herein certain embodiments of the present invention, it is intended that there be covered as well any change or modification therein which may be made without departing from the spirit and scope thereof.

What is claimed is:

1. A liquid composition consisting essentially of a normally solid nonionic polyoxyalkylene block copolymer and ethylene glycol.

2. A composition of matter consisting essentially of from about 15 to 90 percent by weight of a nonionic polyoxyalkylene block copolymer, 15 to 80 percent by weight ethylene glycol and 0 to 30 percent by weight water.

3. The composition of claim 2 wherein said nonionic copolymer is a cogeneric mixture of conjugated polyoxyalkylene compounds containing in their structure the residue of an active hydrogen containing compound having from 1 to 6 carbon atoms and at least one hydrophobic oxyalkylene chain in which the oxygen/carbon atom ratio does not exceed 0.4 and at least one hydrophilic oxyalkylene chain in which the oxygen/carbon atom ratio is greater than 0.4.

4. The composition of claim 3 wherein said nonionic copolymer corresponds to the formula:

$$Y[(C_3H_6O)_n(C_2H_4O)_mH]_x$$

wherein Y is the residue of an organic compound having from about 1 to 6 carbon atoms and containing x reactive hydrogen atoms in which x has a value of at least one, m has a value such that the oxyethylene content of the molecule is from about 20 to 90 weight percent and n has a value such that the total molecular weight of the polyoxypropylene groups is from about 950 to 4000.

5. The composition of claim 4 wherein Y is a residue of propylene glycol and x is 2.

6. The composition of claim 4 wherein Y is the residue of ethylene diamine and x is 4.

7. The composition of claim 3 wherein said nonionic copolymer corresponds to the formula:

$$Y[(C_2H_4O)_m(C_3H_6O)_nH]_x$$

wherein Y is the residue of an organic compound having from about 1 to 6 carbon atoms and containing x reactive hydrogen atoms in which x has a value of at least one, m has a value such that the oxyethylene content of the molecule is from about 20 to 90 weight percent and n has a value such that the total molecular weight of the polyoxypropylene groups is from about 950 to 4000.

8. The composition of claim 7 wherein Y is the residue of ethylene glycol and x is 2.

9. The composition of claim 7 wherein Y is the residue of ethylene diamine and x is 4.

10. The method for preparing a liquid composition suitable for use in flowable pesticides comprising dissolving a normally solid nonionic polyoxyalkylene block copolymer in ethylene glycol at a temperature of at least about 170° F.

11. The method of claim 10 wherein about 15 to 90 percent by weight of said nonionic copolymer is dissolved in 15 to 80 percent by weight ethylene glycol and 0 to 30 percent by weight water.

12. The method of claim 11 wherein said nonionic copolymer is a cogeneric mixture of conjugated polyoxyalkylene compounds containing in their structure the residue of an active hydrogen containing compound having from 1 to 6 carbon atoms and at least one hydrophobic oxyalkylene chain in which the oxygen/carbon atom ratio does not exceed 0.4 and at least one hydrophilic oxyalkylene chain in which the oxygen/carbon atom ratio is greater than 0.4.

13. The method of claim 12 wherein said nonionic copolymer corresponds to the formula:

$$Y[(C_3H_6O)_n(C_2H_4O)_mH]_x$$

wherein Y is the residue of an organic compound having from about 1 to 6 carbon atoms and containing x reactive hydrogen atoms in which x has a value of at least one, m has a value such that the oxyethylene content of the molecule is from about 20 to 90 weight percent and n has a value such that the total molecular weight of the polyoxypropylene groups is from about 950 to 4000.

14. The method of claim 13 wherein y is a residue of propylene glycol and x is 2.

15. The method of claim 13 wherein Y is the residue of ethylene diamine and x is 4.

16. The method of claim 12 wherein said nonionic copolymer corresponds to the formula:

$$Y[(C_2H_4O)_m(C_3H_6O)_nH]_x$$

wherein Y is the residue of an organic compound having from about 1 to 6 carbon atoms and containing x reactive hydrogen atoms in which x has a value of at least one, m has a value such that the oxyethylene content of the molecule is from about 20 to 90 weight percent and n has a value such that the total molecular weight of the polyoxypropylene groups is from about 950 to 4000.

17. The method of claim 16 wherein Y is the residue of ethylene glycol and x is 2.

18. The method of claim 16 wherein Y is the residue of ethylene diamine and x is 4.

* * * * *

REEXAMINATION CERTIFICATE (733rd)
United States Patent [19]
Kaneko

[11] B1 4,351,753
[45] Certificate Issued Jul. 28, 1987

[54] LIQUIFIED NORMALLY SOLID POLYOXYALKYLENE BLOCK COPOLYMERS

[75] Inventor: Thomas M. Kaneko, Trenton, Mich.

[73] Assignee: BASF Wyandotte Corporation, Wyandotte, Mich.

Reexamination Request:
No. 90/001,112, Oct. 6, 1986

Reexamination Certificate for:
Patent No.: 4,351,753
Issued: Sep. 28, 1982
Appl. No.: 200,118
Filed: Oct. 24, 1980

[51] Int. Cl.$^4$ .................. B01F 17/00; C08K 5/05; C07C 43/11; C08L 63/00
[52] U.S. Cl. .................. 252/357; 252/351; 252/352; 524/386; 524/612; 568/613; 568/620
[58] Field of Search .............. 524/386, 612; 252/352, 252/351, 357

[56] References Cited

U.S. PATENT DOCUMENTS

| | | | |
|---|---|---|---|
| 3,630,973 | 12/1971 | Ardla | 260/2.5 |
| 4,043,752 | 8/1977 | Kilmurry et al. | 8/41 B |
| 4,273,884 | 6/1981 | Dominguez | 521/114 |

FOREIGN PATENT DOCUMENTS

190210  9/1981  Czechoslovakia .
380681  5/1973  U.S.S.R. .

OTHER PUBLICATIONS

Pluronic Polyols Toxicity and Irritation Data; Wyandotte Chemicals Corp.; 1967.
The Wonderful World of Pluronic Polyols; BASF Wyandotte Corp.; 1973.
Nonionic Surfactants; Martin J. Schick; Pub. by Marcel Dekker, Inc.
Wyandotte Technical Bulletin; Toxicity and Irretation *Data on the Pluronics*; 1952, reprinted 1955.
Merck Index; 10th edition, #3744; p. 550; 1983, Oct.

*Primary Examiner*—L. T. Jacobs

[57] ABSTRACT

This invention relates to liquified normally solid forms of polyoxyalkylene block copolymers particularly suitable for use in pesticide concentrates comprising a normally solid polyoxyalkylene block copolymer nonionic surface-active agent and ethylene glycol with or without water.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10-18 is confirmed.

Claim 1 is cancelled.

Claim 2 is determined to be patentable as amended.

Claims 3-9, dependent on an amended claim, are determined to be patentable.

New claims 19 and 20 are added and determined to be patentable.

2. A *liquid* composition of matter consisting essentially of from about 15 to 90 percent by weight of a *normally solid* nonionic polyoxyalkylene block copolymer, 15 to 80 percent by weight ethylene glycol and 0 to 30 percent by weight water.

*19. A liquid composition of matter consisting essentially of from about 20 to 80 percent by weight of a normally solid nonionic polyoxyalkylene block copolymer, 20 to 60 percent by weight ethylene glycol and 5 to 20 percent by weight water.*

*20. A liquid composition of matter consisting essentially of from about 20 to 80 percent by weight of a normally solid nonionic polyoxyalkylene block copolymer, 20 to 60 percent by weight ethylene glycol and 5 to 30 percent by weight water.*

* * * * *